(12) United States Patent
Tsutamori et al.

(10) Patent No.: US 6,343,142 B1
(45) Date of Patent: Jan. 29, 2002

(54) IMAGE ANALYZING APPARATUS

(75) Inventors: Yasuhiro Tsutamori; Takashi Kaneko, both of Kanagawa-ken (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 08/433,642

(22) Filed: May 4, 1995

(30) Foreign Application Priority Data

May 20, 1994 (JP) ............................................. 6-130940
May 25, 1994 (JP) ............................................. 6-133889

(51) Int. Cl.⁷ ................................................. G06K 9/00
(52) U.S. Cl. ............................ 382/128; 250/483; 378/4
(58) Field of Search ..................... 395/155; 364/927.2, 364/927.4; 382/130, 132, 171, 173, 180, 128–129, 133–134; 358/520; 250/583; 435/6; 436/86; 378/4

(56) References Cited

U.S. PATENT DOCUMENTS

| | | | |
|---|---|---|---|
| 4,777,597 A | * 10/1988 | Shiraishi et al. | 382/323 |
| 4,865,967 A | 9/1989 | Shiraishi et al. | 435/6 |
| 5,012,333 A | * 4/1991 | Lee et al. | 358/520 |
| 5,012,521 A | * 4/1991 | Endo et al. | 382/322 |
| 5,028,793 A | 7/1991 | Lindmayer et al. | 250/484.1 |
| 5,260,190 A | 11/1993 | Shiraishi et al. | 435/6 |
| 5,270,162 A | 12/1993 | Shiraishi et al. | 435/6 |
| 5,420,628 A | * 5/1995 | Poulsen et al. | 382/128 |

FOREIGN PATENT DOCUMENTS

| | | | |
|---|---|---|---|
| GB | A2246197 | 1/1992 | G01N/21/76 |
| JP | 5915843 | 1/1984 | G01N/23/20 |
| JP | 6151738 | 3/1986 | H01J/37/22 |
| JP | 6193538 | 5/1986 | H01J/37/20 |

* cited by examiner

Primary Examiner—Jayanti K. Patel
(74) Attorney, Agent, or Firm—Sughrue Mion, PLLC

(57) ABSTRACT

An image analyzing apparatus includes an image data memory for storing image data, a display for displaying an image based on image data selected from the image data stored in the image data memory and processed in a predetermined manner, a graphic data memory for storing graphic data corresponding to a plurality of patterns to be displayed on the display, a quantitative processing section for quantitatively processing image data corresponding to the images contained in regions of interest defined by the patterns, a quantitative data memory for storing quantitative data produced by the quantitative processing section, and a background management section for producing and storing background data relating to background values corresponding to noise components for each of the patterns. According to the thus constituted image analyzing apparatus, it is possible to accurately and smoothly quantitatively process and analyze an image contained in a region of interest defined by a pattern.

31 Claims, 11 Drawing Sheets

FIG. 4(a)

| No. | PATTERN TYPE | COORDINATE DATA |
|---|---|---|
| 1 | RECTANGULAR PATTERN | $x_1=, y_1=, \cdots$ |
| 2 | RECTANGULAR PATTERN | $x_2=, y_2=, \cdots$ |
| 3 | RECTANGULAR PATTERN | $x_3=, y_3=, \cdots$ |
| 4 | CIRCULAR PATTERN | $x_4=, y_4=, \cdots$ |
| 5 | CIRCULAR PATTERN | $x_5=, y_5=, \cdots$ |
| 6 | CIRCULAR PATTERN | $x_6=, y_6=, \cdots$ |
| $\cdots$ | $\cdots$ | |
| n | | |

FIG. 4(b)

| No. | PSL VALUE | AREA |
|---|---|---|
| 1 | 934.66 | 74.36 |
| 2 | 2551.79 | 74.36 |
| 3 | 1135.05 | 74.36 |
| 4 | 89.88 | 35.76 |
| 5 | 74.88 | 29.82 |
| 6 | 65.38 | 25.04 |
| $\cdots$ | $\cdots$ | $\cdots$ |
| n | | |

201: GRAPHIC DATABASE

| No. | PATTERN TYPE | COORDINATE DATA |
|---|---|---|
| 1 | CIRCULAR PATTERN | x₁ = **, ··· |
| 2 | CIRCULAR PATTERN | x₂ = **, ··· |
| 3 | RECTANGULAR PATTERN | x₃ = **, ··· |
| ⋮ | ⋮ | ⋮ |
| n | RECTANGULAR PATTERN | xₙ = **, ·· |

202: QUANTITATIVE DATABASE

| VALUE | AREA | GROUP | BACKGROUND |
|---|---|---|---|
| ** | *** | A | 1 |
| ** | *** | B | 2 |
| ** | *** | A | 1 |
| | | ⋮ | |
| ** | *** | B | 2 |

203 → No. column
204 → PATTERN TYPE column
205 → COORDINATE DATA column
206 → VALUE column
207 → AREA column
208 → GROUP column
209 → BACKGROUND column
210

IMAGE ANALYZING APPARATUS

BACKGROUND OF THE INVENTION

The present invention relates to an image analyzing apparatus and, particularly, to such an apparatus for quantitatively analyzing an image included in a region of interest.

DESCRIPTION OF THE PRIOR ART

Various image analyzing methods are known. These include an autoradiographic process comprising the steps of introducing a radioactively labeled substance into an organism, using the organism or a part of the tissue of the organism as a specimen, placing the specimen and a radiographic film such as a high sensitivity type X-ray film together in layers for a certain period of time to expose the radiographic film thereto and obtaining locational information regarding the radioactively labeled substance in the specimen from the resolved pattern of the radiographic film, a chemiluminescent process comprising the steps of selectively labeling a fixed high molecular substance such as a protein or a nucleic acid sequence with a labeling substance which generates chemiluminescent emission when it contacts a chemiluminescent substance, contacting the high molecular substance selectively labeled with the labeling substance and the chemiluminescent substance, detecting the chemiluminescent emission in the wavelength of visible light generated by the contact of the chemiluminescent substance and the labeling substance and obtaining information relating to the high molecular substance such as genetic information, a detecting method using an electron microscope comprising the steps of irradiating a metal or nonmetal specimen with an electron beam, detecting a diffraction image, transmission image or the like and effecting elemental analysis, composition analysis of the specimen, structural analysis of the specimen or the like, or irradiating the tissue of an organism with an electron beam and detecting an image of the tissue of the organism, and a radiographic diffraction image detecting process comprising the steps of irradiating a specimen with radiation, detecting a radiographic diffraction image and effecting structural analysis of the specimen or the like.

Conventionally, these methods are carried out by employing a photographic film as a detecting material, recording a radiographic image, a chemiluminescent image, an electron microscopic image, a radiographic diffraction image or the like on the photographic film and observing a visual image with the eyes. However, in the case where a photographic film is employed as a detecting material, since a radiographic film has low sensitivity, there is a problem that it takes considerable time for recording an image in the autoradiographic process and the radiographic diffraction image detecting process. Further, in the chemiluminescent process, although it is necessary to employ a highly sensitive film having a high gamma value for detecting very weak chemiluminescent emission, when the highly sensitive film having a high gamma value is employed, it is difficult to expose the film reliably using a straight portion of the characteristic curve. Therefore, the film is often exposed improperly and it is necessary to repeatedly expose the films. Moreover, in the detecting process using the electron microscope, since the straight portion of the characteristic curve of a photographic film for an electron microscope is short, it is difficult to determine the proper exposure condition and it is necessary to repeatedly expose the films. Furthermore, in either processes, it is indispensable to chemically develop the films and, therefore, the operations are unavoidably complicated.

In view of the above, there have been proposed an autoradiographic process, a chemiluminescent process, a detecting process using an electron microscope and a radiographic diffraction image detecting process comprising the steps of employing, as a detecting material for the radiation, the visible light, the electron beam or the like, not a photographic film, but a stimulable phosphor which can absorb and store the energy of radiation, visible light, an electron beam or the like upon being irradiated therewith and release a stimulated emission whose amount is proportional to that of the received radiation, the visible light, the electron beam or the like upon being stimulated with an electromagnetic wave having a specific wavelength range, photoelectrically detecting the stimulated emission released from the stimulable phosphor, converting the detection signal to a digital signal, effecting a predetermined image processing on the obtained image data and reproducing an image on displaying means such as a CRT or the like or a photographic film (See for example, Japanese Patent Publication No. 1-60784, Japanese Patent Publication No. 1-60782, Japanese Patent Publication No. 4-3952, U.S. Pat. No. 5,028,793, UK Patent Application 2,246,197 A, Japanese Patent Application Laid Open No. 61-51738, Japanese Patent Application Laid Open No. 61-93538, Japanese Patent Application Laid Open No. 59-15843 and the like).

According to the detecting processes using the stimulable phosphor, development, which is a chemical processing, becomes unnecessary. In addition, the exposure time can be markedly shortened in the autoradiographic process and the radiographic diffraction image detecting process. Improper exposure becomes rare and the exposing operation becomes easy in the chemiluminescent process and the detecting process using the electron microscope. Further, since the image is reproduced after the detected signal has been converted to a digital signal, the image can be reproduced in a desired manner by effecting signal processing on image data and it is also possible to effect quantitative analysis using a computer. Use of a stimulable phosphor in these process is therefore advantageous.

An image forming/analyzing apparatus for effecting an autoradiographic process, a chemiluminescent process, a detecting process using an electron microscope or a radiographic diffraction image detecting process using stimulable phosphor sheets should preferably be able to define a desired region in image data as a region of interest, evaluate amounts of light emitted from a stimulable phosphor sheet as the density of the pixels constituting an image included in the region of interest, obtain the sum thereof, conduct quantitative processing, group a plurality of regions of interest, calculate the density ratio between the pixels in the regions of interest belonging to any particular group and conduct quantitatively analysis.

For instance, in the thin layer chromatography widely used in research into drug metabolism, for analysis of how a drug labeled with a labeling substance and introduced into a test animal changes in the body of the animal is conducted by collecting specimens of urine, blood, tissue or the like from a specific region of the animal at predetermined time intervals, processing the specimens in a predetermined manner and dropping the processed specimens at predetermined positions at regular intervals on a TLC plate which is formed by coating a glass plate with powders of silica gel. The TLC plate is dipped in a distribution solvent and the specimens are chromatographically distributed, thereby forming separate spots for individual components of the specimens. It is often necessary, based on image data obtained by placing the thus produced TLC plate onto a stimulable phosphor sheet, to define regions corresponding to certain spots as regions of interest, group a plurality of predetermined regions, evaluate the density of each region and obtain ratios between the densities of respective regions belonging to the group.

The image forming/analyzing apparatus for effecting such quantitative processing and analysis normally includes graphic data storing means for storing graphic data such as coordinate data of patterns surrounded by a circle, a rectangle or a broken line used for defining a region of interest. This graphic data storing means is provided independently of image data storing means for storing image data. FIG. 11 is a functional block diagram showing the configuration of a conventional graphic data storing means. As shown in FIG. 11, graphic data storing means 200 stores a graphic database 201 and a quantitative database 202. The graphic database 201 includes pattern number data 203 indicating the pattern numbers, pattern type data 204 indicating pattern types such as circle pattern or rectangular pattern and coordinate data 205 indicating pattern positions on an image. The quantitative database 202 includes density data 206 indicating the signal levels of image data contained in a region defined by patterns, region data 207 indicating pattern areas and group data 208 indicating groups to which patterns belong.

When an operator draws a pattern on the screen of a display means (not shown) using a mouse (not shown), graphic data 210 consisting of the pattern number data 203, the pattern type data 204 and the coordinate data 205 are stored in the graphic database 201. The operator then further operates the mouse in a predetermined manner for calculating the area of the pattern and density data 206 corresponding to the signal levels of the image data enclosed by the region defined by the pattern. The results are stored in the graphic data storing means. Moreover, the group data 208 indicating the group to which the pattern belongs are stored in the graphic data storing means by operating the mouse in a predetermined manner.

Further, for enabling the density data to be more accurately calculated, it is necessary to remove from the density data corresponding to background noise, namely noise components uniformly recorded on the stimulable phosphor sheet by cosmic rays, ground radiation or inherent radiation contained in, for example, the TLC plate onto which the specimens are chromatographically distributed. Therefore, the image forming/analyzing apparatus is constituted so that a pattern can be drawn at a region whose density is to be zero on an image displayed on the display means as a background pattern, that a reference background value, namely, density per unit area, can be calculated based on the density of the pattern and that the density data can be more accurately calculated based on the reference background value. For this purpose, the quantitative data base 202 further includes background number data 209 indicating the pattern numbers produced as background patterns.

The thus produced graphic data 210 are synthesized with image data stored in the image data storing means to be output to display means such as a CRT and the synthesized data are displayed on the screen of the display means. The density of the pixels constituting an image contained in a region defined by a pattern belonging to a particular group, accurate density obtained by removing the background density from the density of the pixels, density ratios between patterns belonging to a certain group or the like are displayed.

However, since only one background pattern is allotted per group in the conventional image forming/analyzing apparatus, a background pattern cannot be determined for each pattern belonging to a group so that an accurate reference background value cannot be obtained for each pattern. In particular, in the case where a plurality of substances are chromatographically distributed by dropping them on different TLC plates whose materials and inherent radiation amounts are different from each other and the distributed substances are transferred onto a stimulable phosphor sheet to obtain image data, if a plurality of patterns defining regions corresponding to spots formed on the different TLC plates are allotted to one group, it is impossible to determine an accurate background value for each of the patterns and to accurately calculate the density of the region defined by each of the patterns.

Further, since each pattern displayed on the display means belongs to only one group, the conventional image forming/analyzing apparatus has the following problem.

Consider, for instance, the case described above in which images obtained by simultaneously dropping a plurality of substances on a TLC plate and chromatographically distributing them thereon are recorded on a stimulable phosphor sheet, thereby obtaining image data, whereafter regions corresponding to positions on the TLC plate where spots are formed are defined as regions of interest and a plurality of regions among these regions are grouped. In this case, if regions corresponding to a plurality of spots contained in an image pattern of one substance are grouped to one group, these regions cannot belong to any group including regions corresponding to spots contained in an image pattern of other substances.

Therefore, for instance, in the case where drugs are introduced to a test animal and tissue of a particular part thereof is collected at predetermined time intervals to be chromatographically distributed, it is impossible to simultaneously obtain an amount ratio between components of the tissue collected at one time and an amount ratio between corresponding components of the tissues collected at a different time and in the case where drugs are introduced into a plurality of test animals and tissues of a particular part thereof are collected to be chromatographically distributed, it is impossible to simultaneously obtain an amount ratio between components of the tissue collected from one test animal and an amount ratio between corresponding components of the tissues collected from a different test animal. Therefore, the images in the regions of interest that were defined by patterns cannot smoothly be analyzed.

The same problems occur in the case where, after recording an autoradiographic image, a chemiluminescent image, an electron microscopic image, a radiographic diffraction image or the like on a photographic film, the recorded image is photoelectrically read and converted to a digital signal and the thus obtained image signal is signal processed in a desired manner, thereby reproducing a visible image on displaying means such as a CRT or a photographic film.

SUMMARY OF THE INVENTION

It is therefore an object of the present invention to provide an image analyzing apparatus which can accurately and smoothly qualitatively process and analyze an image contained in a region of interest defined by a pattern.

The above and other objects of the present invention can be accomplished by an image analyzing apparatus comprising image data storing means for storing image data, display means for displaying an image based on image data selected from the image data stored in the image data storing means and processed in a predetermined manner, graphic data storing means for storing graphic data corresponding to a plurality of patterns to be displayed on the display means, quantitative processing means for quantitatively processing image data corresponding to the images contained in regions of interest defined by the patterns, quantitative data storing means for storing quantitative data produced by the quantitative processing means, and background management means for producing and storing background data relating to background values corresponding to noise components for each of the regions of interest.

In a preferred aspect of the present invention, an image analyzing apparatus further comprises background value producing means for producing the background values based on the background data stored in the background management means and the quantitative data stored in the quantitative data storing means and table data producing means for producing table data including the background value for each of the regions of interest and the display means is adapted to display a table based on the table data.

In a further preferred aspect of the present invention, the graphic data storing means is adapted to store pattern numbers allotted to the patterns defining the regions of interest and the background management means comprises background storing means for storing a pattern number of the pattern defining the region of interest to be processed using the background value.

In a further preferred aspect of the present invention, the background management means is constituted so as to select graphic data corresponding to at least one pattern from the graphic data stored in the graphic data storing means and produce the background data based thereon to produce the background value.

In a further preferred aspect of the present invention, the background management means is adapted to allot a background number to the at least one pattern and the background storing means is adapted to store the pattern numbers in a region of the corresponding background number.

In a further preferred aspect of the present invention, the background value producing means is adapted to produce density data of pixels constituting an image defined by the pattern and area data representing an area of the image and a reference background value per unit area based thereon, thereby producing the background value.

In a further preferred aspect of the present invention, in the case where the background value is produced using a plurality of patterns, the background value producing means is adapted to determine the reference background value by averaging the reference background values of the plurality of patterns.

The above and other objects of the present invention can be also accomplished by an image analyzing apparatus comprising image data storing means for storing image data, display means for displaying an image based on image data selected from the image data stored in the image data storing means and processed in a predetermined manner, graphic data storing means for storing graphic data corresponding to a plurality of patterns to be displayed on the display means, quantitative processing means for quantitatively processing image data corresponding to the images contained in regions of interest defined by the patterns, quantitative data storing means for storing quantitative data produced by the quantitative processing means, and group data storing means for storing group data determined for showing the relationship between the patterns and groups to which the patterns belong.

In a preferred aspect of the present invention, an image analyzing apparatus further comprises table data producing means for producing table data including a ratio of quantitative data for each of the groups based on the group data stored in the group data storing means and quantitative data stored in the quantitative data storing means and the display means is adapted to display a table based on the table data.

In a further preferred aspect of the present invention, the graphic data storing means is adapted to store pattern number data allotted to the patterns defining the regions of interest and coordinate data showing positions of the patterns in the image data and the group data storing means is adapted to store the pattern number data of the patterns belonging to each of the groups.

In a further preferred aspect of the present invention, the table data producing means is adapted to produce table data for each of the groups and the display means is adapted to display a table based on the table data so that data are displayed for each of the pattern number data.

In a further preferred aspect of the present invention, the quantitative data produced by the quantitative data producing means comprise density data of pixels constituting images contained in regions of interest defined by the patterns and area data indicating areas of the regions defined by the patterns.

In a further preferred aspect of the present invention, the image data are produced using a stimulable phosphor sheet.

In a further preferred aspect of the present invention, the image data are constituted by image data selected from a group consisting of autoradiographic image data, radiographic diffraction image data, electron microscopic image data and chemiluminescent image data.

In a further preferred aspect of the present invention, the autoradiographic image data, the radiographic diffraction image data and the electron microscopic image data are produced by absorbing and storing the energy of a radiation or an electron beam emitted from a specimen in a stimulable phosphor, irradiating the stimulable phosphor with an electromagnetic wave and photoelectrically converting light emitted from the stimulable phosphor.

In a further preferred aspect of the present invention, the chemiluminescent image data are produced by absorbing and storing the energy of a visible light emitted from a specimen in a stimulable phosphor, irradiating the stimulable phosphor with an electromagnetic wave and photoelectrically converting light emitted from the stimulable phosphor.

In the present invention, the stimulable phosphor employed for producing an autoradiographic image, a radiographic diffraction image and an electron microscopic image may be of any type insofar as it can store radiation energy or electron beam energy and can be stimulated by an electro-magnetic wave to release the radiation energy or electron beam energy stored therein in the form of light. However, a stimulable phosphor which can be stimulated by light having a visible light wavelength is preferably employed. More specifically, preferably employed stimulable phosphors include alkaline earth metal fluorohalide phosphors $(Ba_{1-x},M^{2+}_x)FX:yA$ (where $M^{2+}$ is at least one alkaline earth metal selected from the group consisting of Mg, Ca, Sr, Zn and Cd; X is at least one halogen selected from the group consisting of Cl, Br and I, A is at least one element selected from the group consisting of Eu, Tb, Ce, Tm, Dy, Pr, He, Nd, Yb and Er; x is equal to or greater than 0 and equal to or less than 0.6 and y is equal to or greater than 0 and equal to or less than 0.2.) disclosed in U.S. Pat. No. 4,239,968, alkaline earth metal fluorohalide phosphors SrFX:Z (where X is at least one halogen selected from the group consisting of Cl, Br and I; and Z is at least one of Eu and Ce.) disclosed in Japanese Patent Application Laid Open No. 2-276997, europium activated complex halide phosphors BaFX·xNaX':aEu$^{2+}$ (where each of X or X' is at least one halogen selected from the group consisting of Cl, Br and I; x is greater than 0 and equal to or less than 2; and y is greater than 0 and equal to or less than 0.2.) disclosed in Japanese Patent Application Laid Open No. 589-56479, cerium activated trivalent metal oxyhalide phosphors MOX:xCe (where M is at least one trivalent metal selected from the group consisting of Pr, Nd, Pm, Sm, Eu, Tb, Dy, Ho, Er, Tm, Yb and Bi; X is at least one halogen selected from the group consisting of Br and I; and x is greater than 0 and less than 0.1.) disclosed in Japanese Patent Application Laid Open No. 58-69281, cerium activated rare earth oxyhalide phosphors LnOX:xCe (where Ln is at least one rare earth element selected from the group consisting of Y, La, Gd and Lu; X is at least one halogen selected from the group consisting of Cl, Br, and I; and x is greater than 0 and equal to or less than 0.1.) disclosed in U.S. Pat. No. 4,539,137 and europium activated complex halide phosphors M$''$FX·aM$^I$X'·bM$^{III}$X''$_2$·cM$^{III}$X'''$_3$·xA:yEu$^{2+}$ (where M$''$ is at least one alkaline earth metal selected from the group consisting of Ba, Sr and Ca; MI is at least one alkaline metal selected from the group consisting of Li, Na, K, Rb and Cs; M$^{III}$ is at least one divalent metal selected from the group consisting of Be and Mg; M$^{III}$ is at least one trivalent metal selected from the group consisting of Al, Ga, In and Tl; A is at least one metal oxide; X is at least one halogen selected from the group consisting of Cl, Br and I; each of X', X'' and X''' is at least one halogen selected from the group consisting of F, Cl, Br and I; a is equal to or greater than 0 and equal to or less than 2; b is equal to or greater than 0 and equal to or less than $10^{-2}$; c is equal to or greater than 0 and equal to or less than $10^{-2}$; a+b+c is equal to or greater than $10^{-2}$; x is greater than 0 and equal to or less than 0.5; and y is greater than 0 and equal to or less than 0.2.) disclosed in U.S. Pat. No. 4,962,047.

In the present invention, the stimulable phosphor employed for producing a chemiluminescent image may be of any type insofar as it can store the energy of light having a visible light wavelength and can be stimulated by an electromagnetic wave to release the energy of light having a visible light wavelength stored therein in the form of light. However, a stimulable phosphor which can be stimulated by light having a visible light wavelength is preferably employed. More specifically, preferably employed stimulable phosphors include metal halophosphates, rare-earth-activated phosphors, aluminate-host phosphors, silicate-host phosphors and fluoride-host phosphors disclosed in UK Patent Application 2,246,197 A.

The above and other objects and features of the present invention will become apparent from the following description made with reference to the accompanying drawings.

BRIEF DESCRIPTION OF THE DRAWINGS

FIG. 4(a) shows the makeup of graphic data and FIG. 4(b) shows the makeup of quantitative data.

FIG. 9 shows an image displayed on a CRT.

FIG. 11 is a functional block diagram showing a conventional graphic data storing means.

DESCRIPTION OF THE PREFERRED EMBODIMENTS

Figure 1:
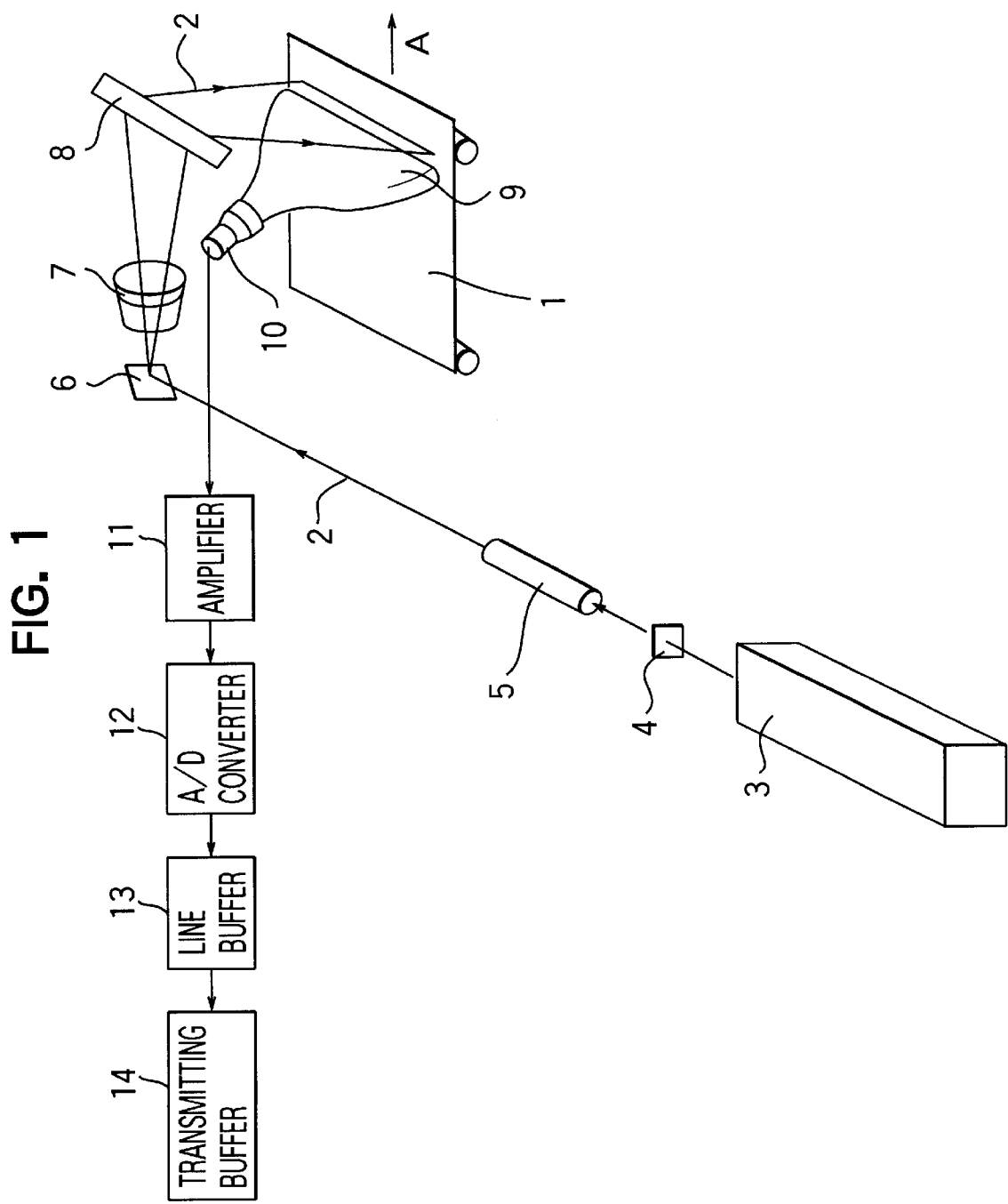
FIG. 1 is a schematic perspective view showing an image reading apparatus for producing image data to be analyzed by an image analyzing apparatus which is an embodiment of the present invention.

A stimulable phosphor sheet 1 shown in FIG. 1 stores locational information regarding radioactive labeling material contained in a specimen (not shown) in the form of radioactive energy. Locational information as termed here includes a variety of information relating to the location of radioactive labeled substances, or aggregations thereof, present in a specimen, such as the location, the shape, the concentration, the distribution or combinations thereof.

In this embodiment, a plurality of drugs whose components were different from each other were introduced into a plurality of test animals and after a predetermined time period was passed, urine was gathered and chromatographically distributed on TLC plate. The thus produced image of a protein is stored in the stimulable phosphor sheet 1.

The stimulable phosphor sheet which stores the locational information regarding a radioactive material in the specimen is scanned with a laser beam 2 and stimulated, thereby being caused to emit stimulated emission.

The laser beam 2 is generated by a laser beam source 3 and passes through a filter 4 to cut off light in the wavelength region corresponding to the wavelength region of stimulated emission to be emitted from the stimulable phosphor sheet 1 in response to stimulation by the laser beam 2. The beam diameter of the laser beam 2 is accurately adjusted by a beam expander 5 and the laser beam 2 enters a beam deflector 6 such as a galvanometer. The laser beam 2 deflected by the beam deflector 6 passes through an fθ lens 7 and is reflected by a plane reflecting mirror 8, thereby impinging upon the stimulable phosphor sheet 1. The fθ lens 7 ensures that the stimulable phosphor sheet 1 is always scanned with the laser beam 2 at a uniform beam speed.

The stimulable phosphor sheet 1 is conveyed in the direction along the arrow in FIG. 1 in synchronism with the above mentioned scanning with the laser beam 2 so that the whole surface of the stimulable phosphor sheet 1 is scanned by the laser beam 2.

When irradiated with the laser beam 2, the stimulable phosphor sheet 1 releases stimulated emission in an amount proportional to the radiation energy stored therein and the stimulated emission enters a light guiding sheet 9.

The light receiving end of the light guiding sheet 9 has a linear shape and is positioned in the vicinity of the stimulable phosphor sheet 1 so as to face the scanning line on the stimulable phosphor sheet 1. The exit end of the light guiding sheet 9 is in the form of a ring and is connected to the light receiving surface of a light detector 10 such as a photomultiplier for photoelectrically detecting light. This light guiding sheet 9 is made by processing a transparent thermoplastic resin sheet such as an acrylic synthetic resin and so constituted that the emission introduced from the light receiving end is transmitted to the exit end under repeated total reflection within the light guiding sheet 9 and received by the light receiving surface of the light detector 10 via the exit end.

Therefore, the stimulated emission produced by the stimulable phosphor sheet 1 upon being irradiated with the laser beam 2 enters into the light guiding sheet 9 and is received by the light detector 10 via the exit end under repeated total reflection within the sheet 9.

On the light receiving surface of the light detector 10 is provided a filter which allows only light of the wavelength region of the stimulated emission released from the stimulable phosphor sheet 1 to pass through and cuts off light of the wavelength region of the laser beam so that the light detector 10 can photoelectrically detect only the stimulated emission released from the stimulable phosphor sheet 1.

The stimulated emission photoelectrically detected by the light detector 10 is converted to an electrical signal, amplified by an amplifier 11 having a predetermined amplifying factor so as to produce an electrical signal of a predetermined level and then input to an A/D converter 12. The electrical signal is converted to a digital signal with a scale factor suitable for the signal fluctuation width and input to a line buffer 13. The line buffer 13 temporarily stores image data corresponding to one scanning line. When the image data corresponding to one scanning line have been stored in the line buffer 13 in the above described manner, the line buffer 13 outputs the data to a transmitting buffer 14 whose capacity is greater than that of the line buffer 13 and when the transmitting buffer 14 has stored a predetermined amount of the image data, it outputs the image data to an autoradiographic image analyzing apparatus.

Figure 2:
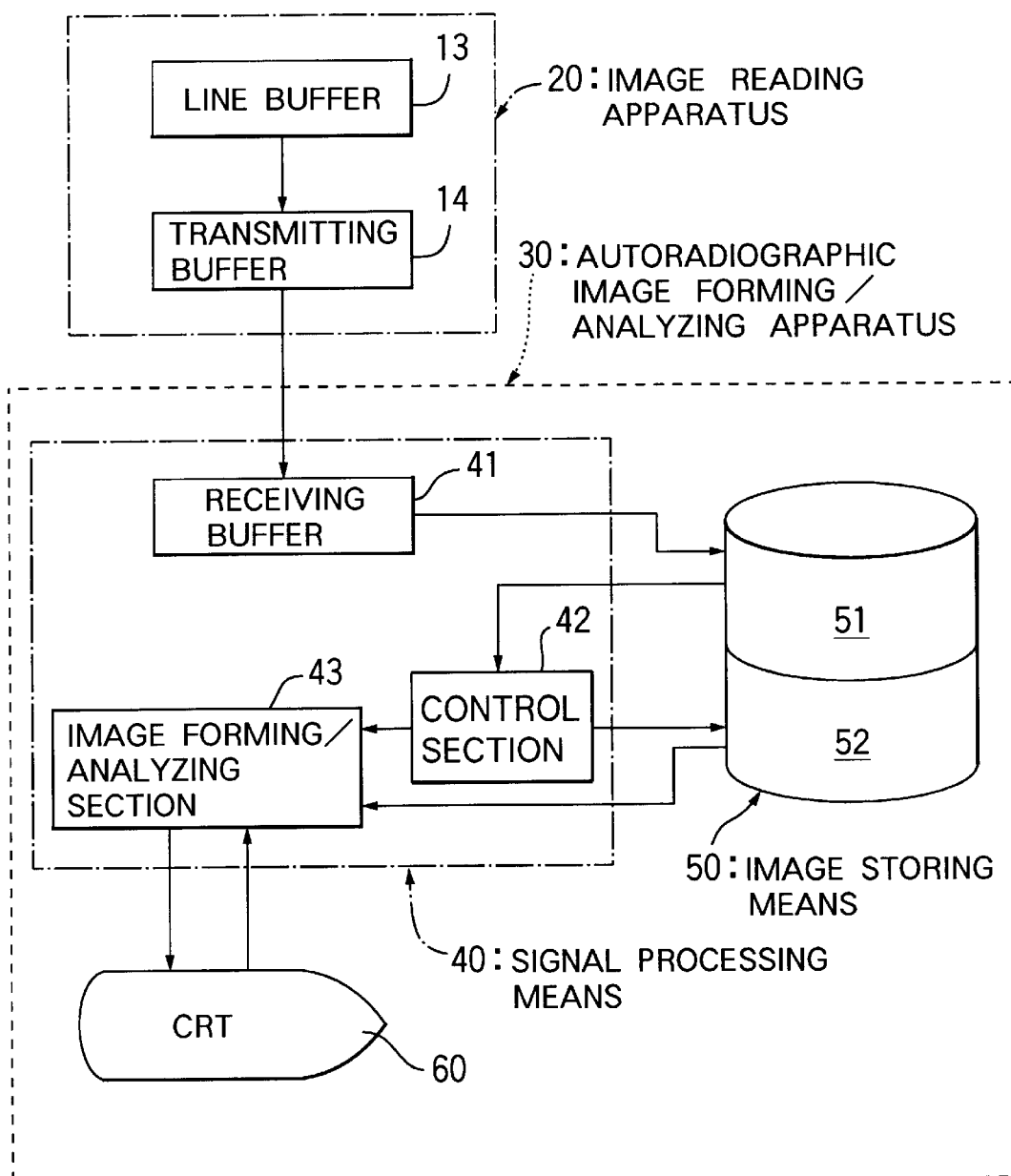
FIG. 2 is a block diagram of an autoradiographic image analyzing apparatus and an image reading apparatus.

FIG. 2 is a block diagram of the autoradiographic image analyzing apparatus and an image reading apparatus.

As shown in FIG. 2, the autoradiographic image analyzing apparatus 30 includes signal processing means 40 for receiving image data containing locational information regarding radioactive labeling material contained in a specimen, which were stored and recorded in the stimulable phosphor sheet 1, read out by the image reading apparatus 20 and converted to a digital signal, and processing them so as to reproduce a visible image which has desirable density, tone, contrast and the like, and has excellent observation and analysis property, image data storing means 50 for storing image data which were input to the signal processing means 40 from the image reading apparatus 20 and processed thereby, and a CRT 60 for reproducing an image based on the image data containing locational information regarding radioactive labeling material contained in a specimen.

The image data temporarily stored in the transmitting buffer 14 of the image reading apparatus 20 are input to a receiving buffer 41 in the signal processing means 40 of the autoradiographic image analyzing apparatus 30 and temporarily stored therein. When a predetermined amount of the image data have been stored, the stored image data are output to an image data temporary storing section 51 in the image data storing means 50 and stored therein. In this manner, the image data fed from the transmitting buffer 14 of the image reading apparatus 20 to the receiving buffer 41 of the signal processing means 40 and temporarily stored therein are fed from the transmitting buffer 14 to the image data temporary storing section 51 in the image data storing means 50. When the image data obtained by scanning the whole surface of the stimulable phosphor sheet 1 with the laser beam 2 have been stored in the image data temporary storing section 51 in the image data storing means 50, the control section 42 in the signal processing means 40 reads the image data from the image data temporary storing section 51 and stores them in an image data storing section 52.

Figure 3:
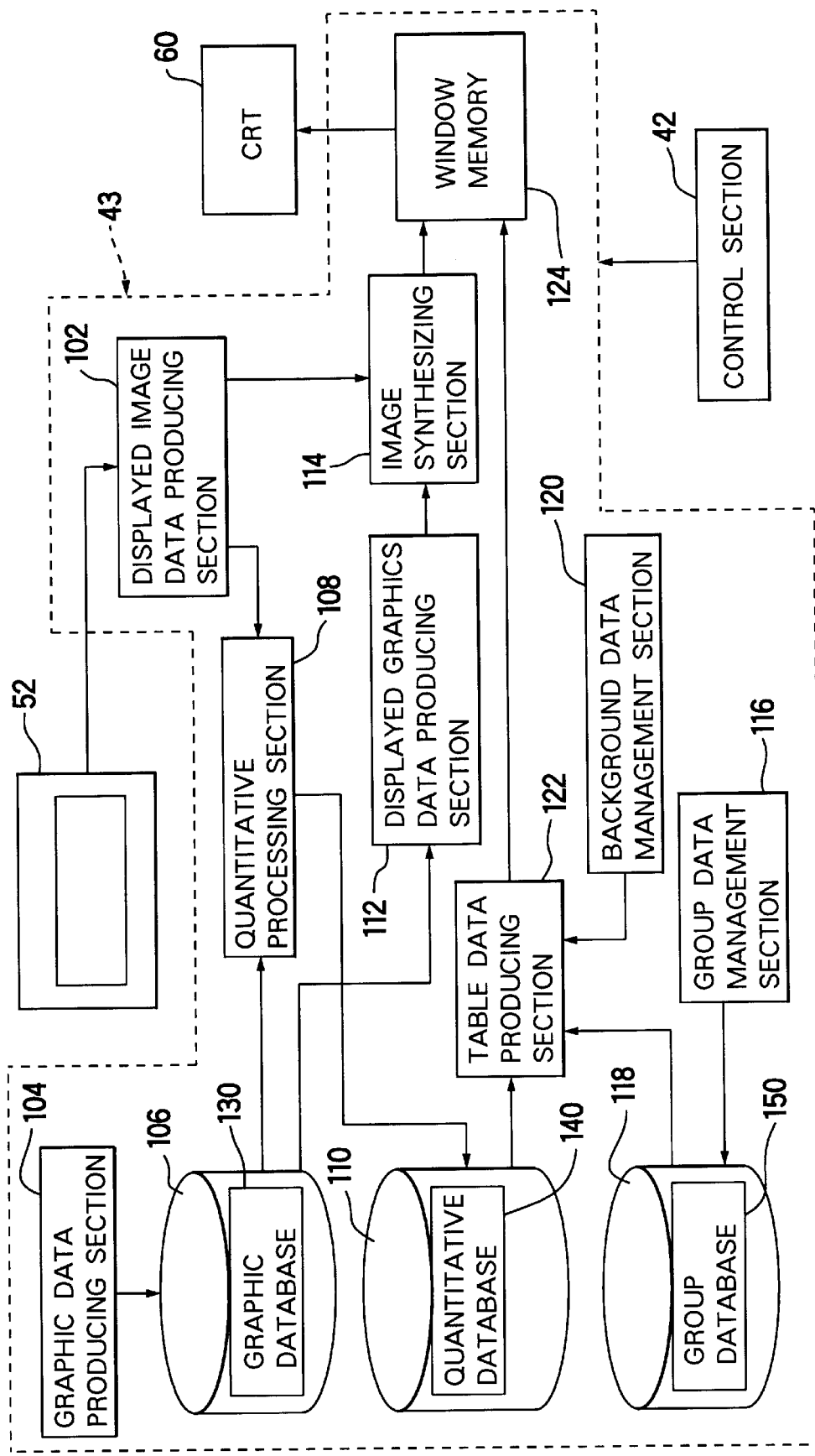
FIG. 3 is a block diagram of an image forming/analyzing section of an autoradiographic image analyzing apparatus which is an embodiment of the present invention and peripheral circuits thereof.

FIG. 3 is a block diagram showing the details of an image forming/analyzing section 43 of the autoradiographic analyzing apparatus 30 which is an embodiment of the present invention and peripheral circuits thereof. As shown in FIG. 3, the image forming/analyzing section 43 includes a displayed image data producing section 102 for processing image data read out from the image data storing section 52 by the operator operating an input device (not shown) in a predetermined manner and producing displayed image data to be displayed on the CRT 60, graphic data producing section 104 for producing graphic data corresponding to patterns such as circular patterns, rectangular patterns and broken line patterns and outputting them to a graphic data storing section 106, the graphic data storing section 106 for storing graphic data, a quantitative processing section 108 for comparing graphic data stored in the graphic data storing section 106 and displayed image data produced by the display image data producing section 102 and producing quantitative data indicating the density of an image contained in a pattern displayed on the screen of the CRT 60, a quantitative data storing section 110 for storing the quantitative data produced by the quantitative processing section 108, a displayed graphics data producing section 112 for producing displayed graphics data to be displayed on the CRT 60, an image synthesizing section 114 for synthesizing the displayed image data and the displayed graphics data, a group data management section 116 for storing group data indicating the group to which the pattern is to belong in a group data storing section 118 in response to the operation of the input device (not shown) by an operator, the group data storing section 118 for storing group data indicating the group to which the pattern is to belong, a background data management section 120 for storing data indicating the pattern selected for generating a reference background value described later, a table data producing section 122 for producing table data based on the data stored in the quantitative data storing section 110, the group data storing section 118 and the background data management section 120, and a window memory 124 for temporarily storing the synthesized image data synthesized by the image synthesizing section 114 and the table data produced by the table data producing section 122 and outputting them to the CRT 60.

The displayed image data producing section 102 is adapted to enlarge or reduce image data read out from the image data storing section 52 in response to the operation of the input device by the operator based on a predetermined magnification factor input by the operator and produce enlarged or reduced displayed image data.

When the operator selects a shape stored as graphic data in a memory (not shown) by operating the mouse (not shown) for enclosing a region of interest of an image displayed on the screen of the CRT 60 and draws the pattern having the selected shape on the screen of the CRT 60, graphic data is produced and stored in the graphic data storing section 106.

The graphic data storing section 106 stores a graphic database 130 comprising graphic data consisting of various patterns having shapes that can be selected by the operator, located at desired positions and stored pattern by pattern. When the operator draws a predetermined pattern on the screen of the CRT 60, the graphic data producing section 104 gives the pattern a pattern number and stores pattern type data indicating the type of the pattern and coordinate data indicating the position of the pattern on the image data stored in the image data storing section 52 in a region corresponding to the pattern number given to the pattern in the graphic database 130. FIG. 4(*a*) shows the makeup of graphic data 132 stored in the graphic database 130 by the graphic data producing section 104. As mentioned above, each item of the graphic data 132 includes at least pattern type data indicating the type of the pattern and coordinate data indicating the position of a reference point of the pattern. In this embodiment, the types of pattern include a circular pattern, a rectangular pattern, a broken line pattern and the like. The coordinate data indicating the reference point of the pattern represents the coordinates (x, y) of the upper left corner of the rectangular pattern circumscribing the pattern on the image data stored in the image data storing section 52.

The graphic data 132 stored in the graphic data storing section 106 are read out to the displayed graphics data producing section 112 and are processed in a predetermined manner. Then, the displayed graphics data are output to the image synthesizing section 114 to be synthesized with the displayed image data and the thus synthesized data are output to the CRT 60 via the window memory 124.

The quantitative data storing section 110 stores a quantitative database 140 comprising quantitative data 142 which, as shown in FIG. 4(*b*), consists of PSL value data 144 corresponding to the density of pixels constituting an image contained in a pattern located on the screen of the CRT 60 and area data 146 indicating the areas of patterns and stored pattern by pattern. The PSL value data 144 represents the accumulated value of radiation on the region of a stimulable phosphor sheet 1 corresponding to the image region surrounded by the pattern.

As described later, when the operator specifies a predetermined pattern by operating an input device (not shown) and inputs an instruction for quantitatively processing the region enclosed by the pattern, the quantitative processing section 108 reads out predetermined graphic data 132 from the graphic database 130 and the region of the image data enclosed by the pattern corresponding to the graphic data from the displayed image data producing section 102 and calculates the area of the pattern and the density of the pixels constituting the image enclosed by the pattern, thereby storing them in a predetermined memory region, namely, a region in the quantitative database 140 corresponding to the pattern number of the graphic data 132 read out from the graphic database 130.

Figure 5:
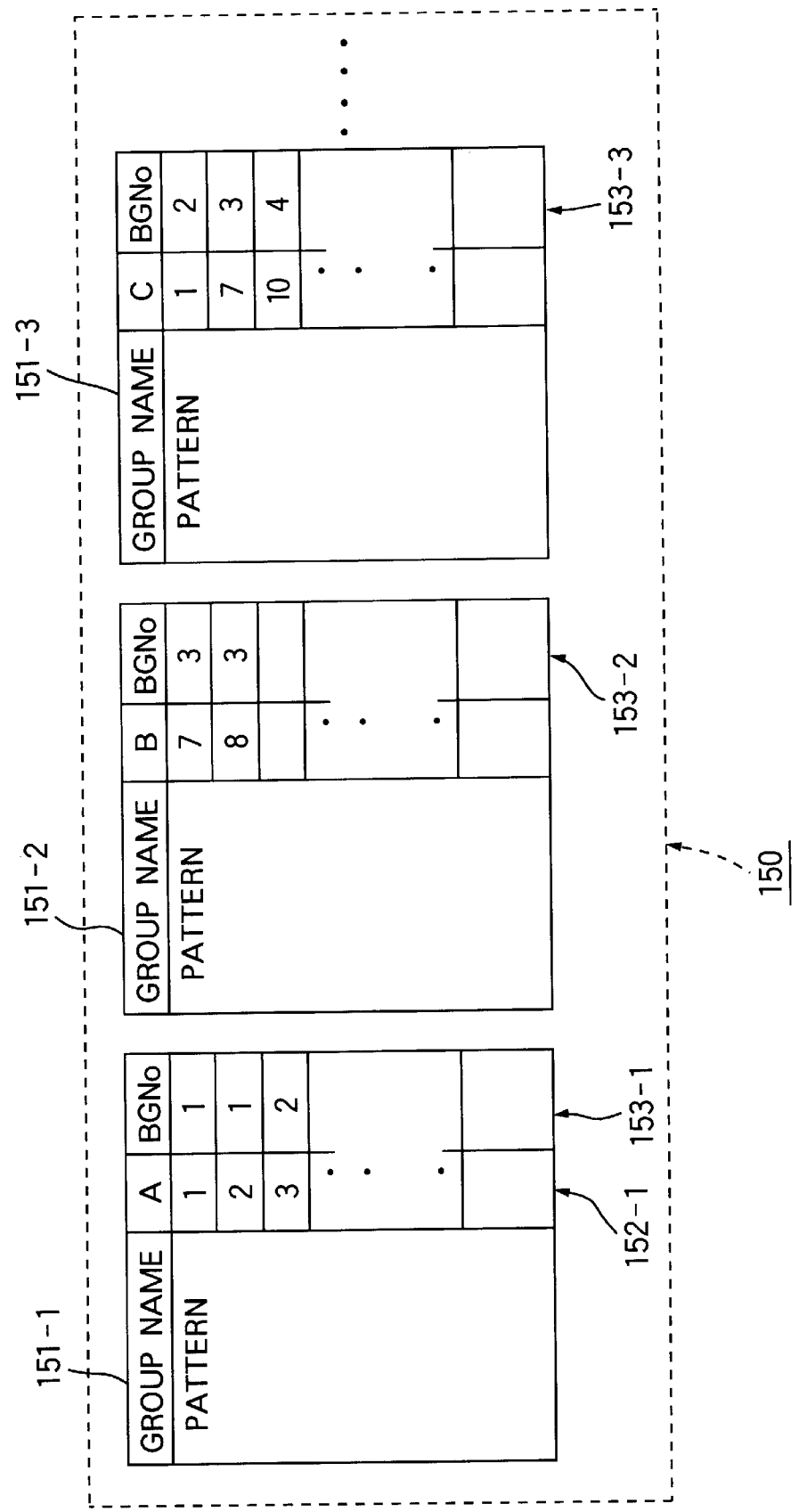
FIG. 5 shows the makeup of a group database.

When the group management section 116 is actuated by operating the input device, a group database 150 is generated in the group data storing section 118. FIG. 5 is a block diagram showing the makeup of the group database 150. As shown in FIG. 5, a plurality of databases 151-1 to 151-3 are generated for the respective groups in the group database 150. Each of the databases 151-1 to 151-3 stores the pattern numbers of the patterns belonging to the group and the numbers of the backgrounds used for calculating the density of the pixels constituting the image contained in the pattern, namely, the background numbers described later.

The thus constituted autoradiographic image analyzing apparatus analyzes an image as follows.

Figure 6:
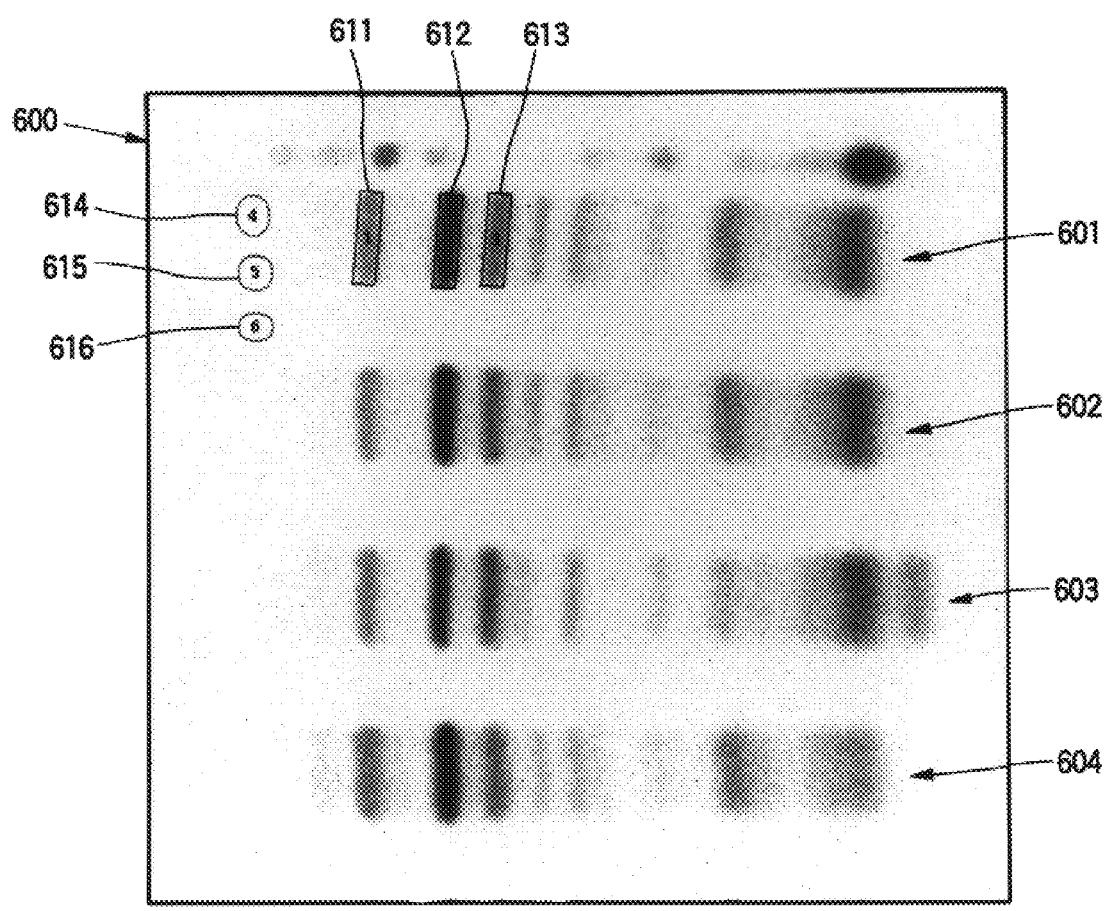
FIG. 6 shows an image displayed on a CRT.

The operator first reads out predetermined image data from the image data storing section 52 by operating a mouse (not shown), thereby producing displayed image data enlarged or reduced by the display data producing section 102 based on a magnification factor selected by the operator. The displayed image data are displayed on the screen 600 of the CRT 60 via the image synthesizing section 114 and the window memory 124. FIG. 6 shows an example of an image displayed on the screen 600 of the CRT 60. In this example, four kinds of drugs whose components were different from each other were introduced into four test animals and, after a predetermined time period, urine was collected from the animals and chromatographically distributed on TLC plate, thereby recording images of proteins in the stimulable phosphor sheet 1 and image data were produced by the image reading apparatus 20. Therefore, image patterns 601, 602, 603 and 604 for four test animals are displayed in four lines on the screen 600 of the CRT 60. When the operator draws a desired pattern in a desired region on the screen 600 of the CRT 60 by operating the mouse, graphic data 132 are stored in the graphic database 130 in the graphic data storing section 106. For instance, as shown in FIG. 6, assuming that patterns 611 to 616 are displayed on the screen 600, the graphic data producing section 104 gives pattern numbers to the patterns in the order that they are displayed and, as shown in FIG. 4(*a*), stores pattern type data and coordinate data of the respective patterns in regions corresponding to the pattern numbers in the graphic database 130. When the operator inputs an instruction for calculating the density of the pixels constituting the image enclosed by each of the patterns by operating the mouse, the quantitative processing section 108 reads out graphic data 132 corresponding to patterns 611 to 616 from the graphic database 130 and reads out displayed image data from the displayed image data producing section 102. Then, the quantitative processing section 108 determines the region of the image data corresponding to the image enclosed by each of the patterns corresponding to the graphic data and calculates the density of the pixels constituting the image enclosed by each of the patterns and the area of each pattern. As shown in FIG. 4(*b*), the thus obtained density of the pixels and the areas of the patterns are stored in the quantitative database 140 as quantitative data consisting of PSL value data 144 and area data 146.

When the operator actuates the group management section 116 by operating an input device (not shown), a group database is produced for each group to which the patterns drawn on the screen 600 of the CRT 60 belong. For instance, when the operator specifies that the patterns 611, 612 and 613 shown in FIG. 6 belong to a group A, then, as shown in FIG. 5, database 151-1 relating to the group A is generated and the pattern numbers "1", "2" and "3" belonging to the group A are stored in a region 152-1 for the database 151-1. Since no background number has yet been specified at this time, no data are stored in a region 153-1 where the background numbers are to be stored so as to correspond to the pattern numbers of the patterns 611 to 613.

Further, the operator actuates the background number management section 120 by operating the input device to select background patterns (hereinafter referred to as "BG patterns") for calculating reference background values from among the patterns 611 to 616.

Figure 7:
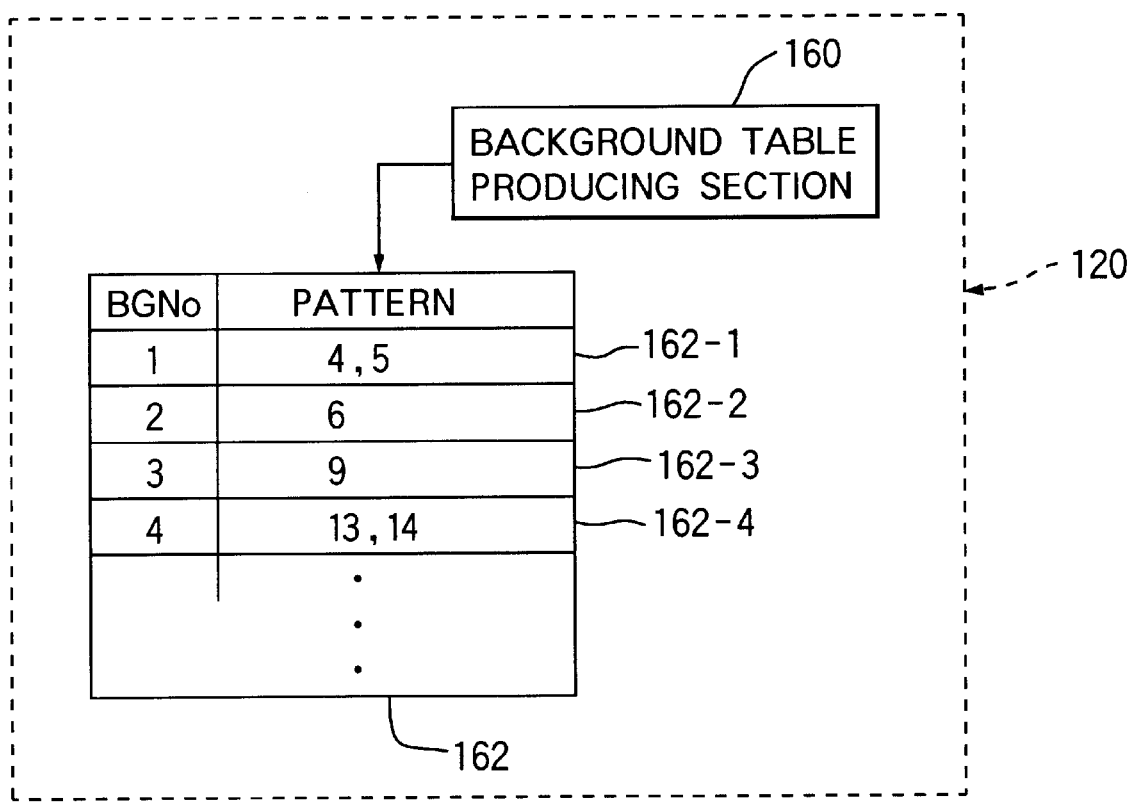
FIG. 7 is a functional block diagram showing a background data management section.

FIG. 7 is a functional block diagram showing the configuration of the background data management section 120. As shown in FIG. 7, the background data management section 120 comprises a background table producing section 160 and a background table 162. The background table 162 is constituted so that each background number stores the pattern numbers of patterns belonging thereto. The background is a noise component uniformly produced on the stimulable phosphor sheet 1 by cosmic rays or ground radiation when the stimulable phosphor sheet 1 is exposed. It is necessary for quantitatively processing image data obtained using the stimulable phosphor sheet 1 to remove the noise component and calculate the density of the pixels constituting the image enclosed by the pattern. For this purpose, in this embodiment, a BG pattern is selected by defining an appropriate region in the image portion where no spot is formed using a pattern and a reference background value is obtained by dividing the PSL value within the region by the area of the pattern. Therefore, the reference background value represents an amount of radiation caused by the noise component per unit area.

In the case where a plurality of patterns belong to a certain background number, the reference background value can be obtained by dividing the sum of the PSL values within the plurality of patterns by the sum of the areas of the patterns.

For instance, if the patterns 614 and 615 shown in FIG. 6 are selected as a BG pattern and the operator allots these patterns to patterns belonging to the background number "1", the background table producing section 162 stores the pattern numbers "4" and "5" of the graphic data corresponding to the patterns 614 and 615 in a predetermined region 162-1 in the background table 162. Similarly, if the pattern 616 is selected as a BG pattern and the operator allots it to the pattern belonging to the background number "2", the background table producing section 162 stores the pattern number 6 of the graphic data corresponding to the pattern 616 in a predetermined region 162-2 in the background table 162.

Figure 8:
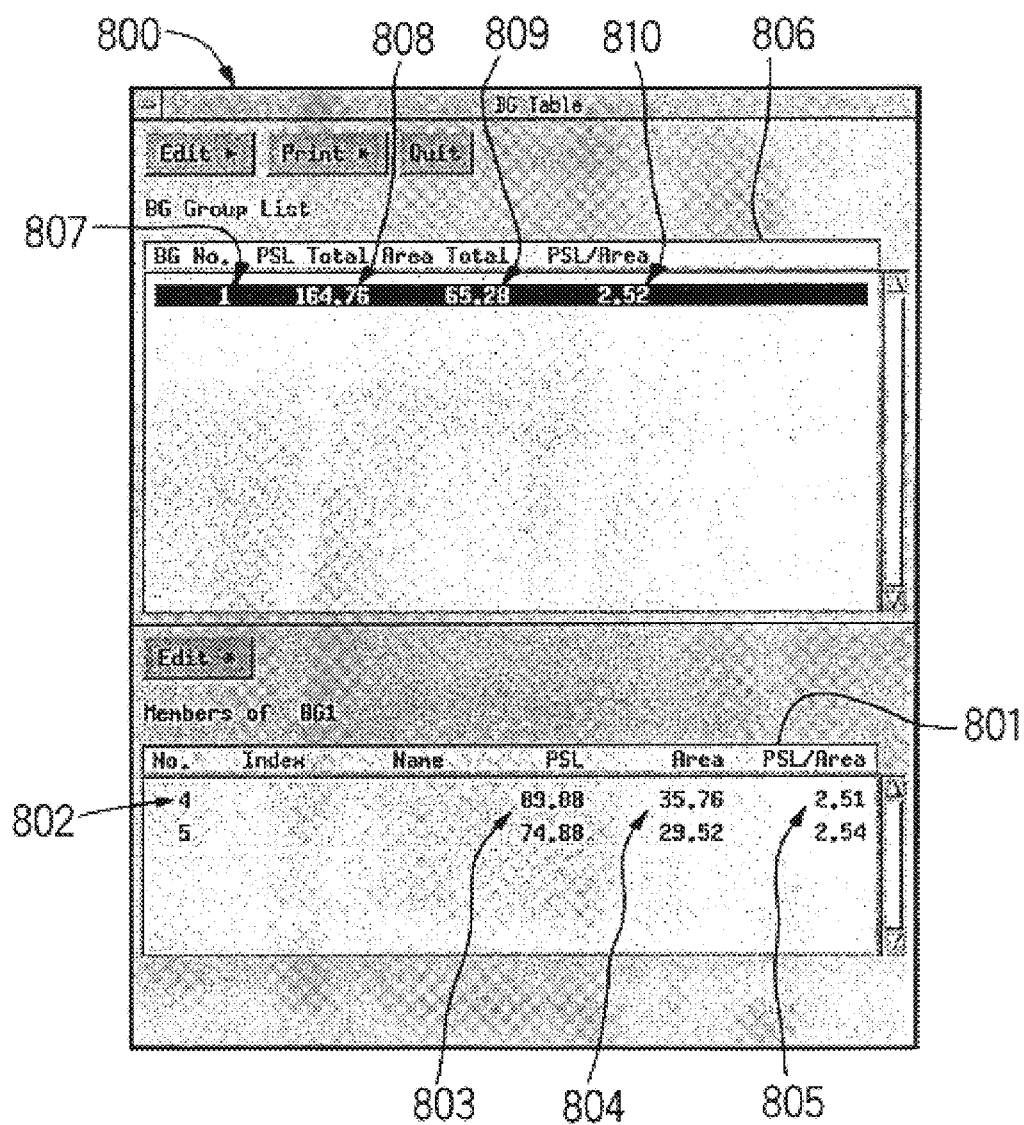
FIG. 8 shows an image displayed on a CRT.
Figure 10:
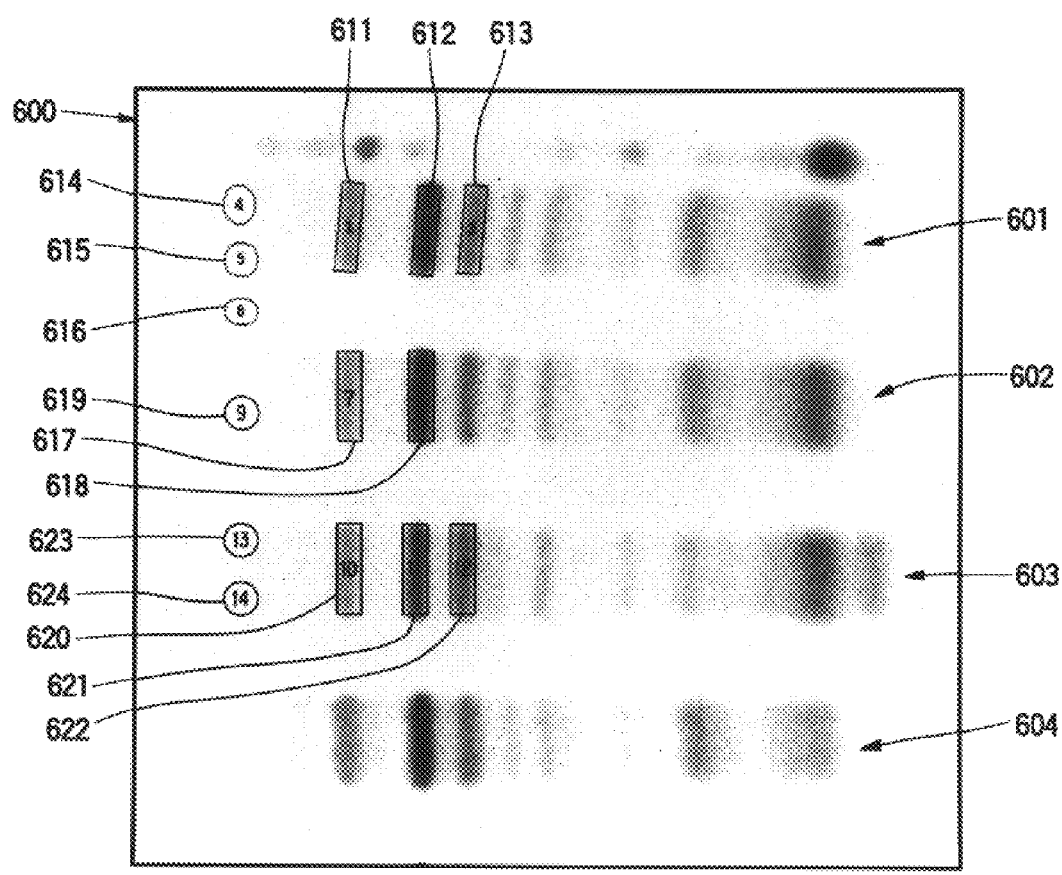
FIG. 10 shows an image displayed on a CRT.

When the BG patterns have been determined in this manner, the table data producing section 122 reads out data from the background table 162 in the background data management section 120 and data from the quantitative database 140 in the quantitative data storing section 110 and calculates the reference background value corresponding to a certain background number based on the PSL value(s) and the area(s) to produce table data corresponding to a table including the reference background value, thereby mapping them in a predetermined region in the window memory 124. The window memory 124 outputs the mapped table data to the CRT 60 at a predetermined time. Therefore, for example, when the patterns 614 and 615 shown in FIG. 6 are selected as a BG pattern and the operator allots these patterns to patterns belonging to the background number "1", the image shown in FIG. 8 is displayed on the screen of the CRT 60. The pattern numbers "4" and "5" of the patterns 614 and 615 selected as a BG pattern, the respective PSL values, the areas thereof and the PSL values per unit area are displayed at regions 802 to 805 in the lower portion 801 of the screen 800 and the background number "1", the sum of the PSL values of the patterns 614 and 615, the sum of the areas thereof and the value obtained by dividing the sum of the PSL values by the sum of the areas, namely, the reference background value, are displayed at regions 807 to 810 in the upper portion of the screen 800.

Then, when the operator starts the quantitative processing, he or she selects a pattern to be quantitatively processed and a background number having a reference background value to be used for quantitative processing. As a result, the group management section 116 stores a predetermined background number(s) in a region(s) 153-1 to 153-3 in the group database 150 where the background numbers of a predetermined database(s) 151-1 to 151-3 are to be stored. For instance, if the operator instructs that the reference background value calculated based on the patterns 614 and 615 should be used for the patterns 611 and 612 belonging to the group A and that the reference background value calculated based on the pattern 616 should be used for the pattern 613, the background number "1" is allotted to the pattern numbers "1" and 11211 stored in a region 152-1 of the database 151-1 and the background number "2" is allotted to the pattern number "3". Thus, as shown in FIG. 5, the background numbers are stored in a region 153-1.

In this way, a desired background number is allotted to each pattern and background numbers are stored in regions 153-1 to 153-3 of the databases 151-1 to 151-3.

Figure 9:
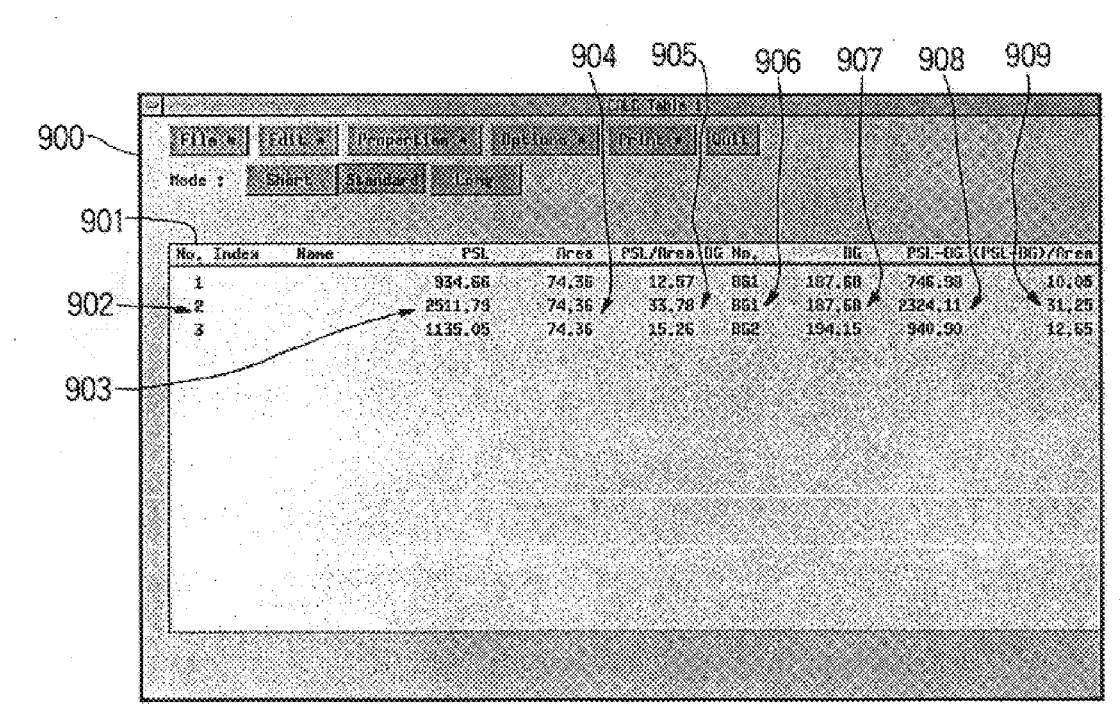

The table producing section 122 reads out data from the background table 162 in the background data management section 120 and data from the quantitative database 140 in the quantitative data storing section 110 and calculates the reference background value corresponding to a certain background number based on the PSL value(s) and the area(s). Further, the table producing section 122 calculates the product of the area of the pattern and the reference background value of the background number allotted to the pattern and subtracts the product from the PSL value of the pattern to obtain a corrected PSL value. Then, the table producing section 122 produces table data using these values and maps them in a predetermined region of the window memory 124. The window memory 124 outputs the mapped table data to the CRT 60 at a predetermined time. For example, when the operator instructs that the reference background value calculated based on the patterns 614 and 615 should be used for the patterns 611 and 612 and the reference background value calculated based on the pattern 616 should be used for the pattern 613, the image shown in FIG. 9 is displayed on the screen 900 of the CRT 60. As shown in FIG. 9, the pattern numbers, PSL values, areas, PSL values per unit area, allotted background numbers, the products of the reference background values and the areas, the differences between the PSL values and the reference background values, namely, the corrected PSL values, and corrected PSL values per unit area are displayed in regions 902 to 909 of a portion 901 in the screen 900.

Further, the table data producing section 122 is constituted so as to be able to effect quantitative analysis in accordance with the instruction of the operator. More specifically, it is possible to calculate a ratio of a PSL value or a corrected PSL value of each pattern to the sum of PSL values of the patterns belonging to a certain group, a ratio of a PSL value per unit area or a corrected PSL value per unit area of respective patterns belonging to a certain group to a PSL value per unit area or a corrected PSL value of a particular pattern belonging to the group or the like and display them on the screen of the CRT 60 via the window memory 124.

As described above, it is possible by operating the input device to define regions of interest in image patterns 601 to 604 using patterns 611 to 624, produce graphic data, select patterns 614 and 615 as a BG pattern belonging to the background number "1", a pattern 616 as a BG pattern belonging to the background number "2", a pattern 619 as a BG pattern belonging to the background number "3" and patterns 623 and 624 as a BG pattern belonging to the background number "4" and produce the background table 162 shown in FIG. 7. Further, as shown in FIG. 5, it is possible to produce the databases 151-1 to 151-3 in the group database 150 by making patterns 611, 612 and 613 belong to a group A, patterns 617 and 618 belong to a group B and patterns 611, 617 and 620 belong to a group C.

In the example shown in FIG. 5, patterns 611, 612 and 613 belong to a group A. This is because each component of an image pattern 601 obtained by collecting and chromatographically distributing urine from the same test animal is grouped to one group. On the other hand, patterns 611, 617 and 620 belong to a group C. This is because spots representing the corresponding components among components chromatographically distributed are grouped to one group. In this way, according to this embodiment, since one pattern can belong to a plurality of groups, it is possible, for instance, to calculate a ratio between respective components containing tissue gathered from the same test animal or calculate a ratio between the corresponding components contained in tissue gathered from a plurality test animals.

Further, according to this embodiment, a background number can be allotted independently to each pattern belonging to each group. For example, as shown in FIG. 7, it is possible to allot a background number "1" to patterns 611 and 612 belonging to a group A, a background number "2" to a pattern 613 belonging to a group A and a pattern 611 belonging to groups A and C, a background number "3" to a pattern 617 belonging to a group B and a background number "5" to a pattern 620 belonging to a group C. Therefore, since a desired background number can be allotted to each pattern independently of the group, the corrected PSL value can be more accurately calculated.

The present invention has thus been shown and described with reference to specific embodiments. However, it should be noted that the present invention is in no way limited to the details of the described arrangements but changes and modifications may be made without departing from the scope of the appended claims.

For example, in the above described embodiment, although the image of a protein produced by thin layer chromatography (TLC) is analyzed, the present invention is not limited to such autoradiography and can also be applied to analyze autoradiographic images such as an autoradiographic image of a gene produced by the Southern blotting method and the hybridization method, an autoradiographic image produced by polyacrylamide gel electrophoresis for the separation or identification of protein or the estimation of molecular weight or properties of protein or the like, an autoradiographic image for studying the metabolism, absorption, excretion path and state of a substance introduced into a test animal such as a mouse. Further, the present invention is applicable for analyzing chemiluminescent images produced by a chemiluminescent process such as a chemiluminescent image of a gene produced by the Southern blot hybridization method, a chemiluminescent image of a protein produced by thin layer chromatography, a chemiluminescent image produced by polyacrylamide gel electrophoresis for the separation or identification of a protein or the estimation of molecular weight or properties of a protein or the like. Moreover, the present invention can be widely applied to the analysis of an electron beam transmission image or an electron beam diffraction image of a metal or nonmetal produced by an electron microscope, an electron beam image of tissue of an organism and a radiographic diffraction image of a metal or nonmetal.

Further, in the above described embodiment, although the background table is constituted so that each background number stores the pattern numbers of BG patterns belonging thereto and the table data producing section 122 calculates reference background values, the background table 162 may be constituted so that each background number stores a reference background value.

Furthermore, in the above described embodiment, although the quantitative database 140 stores PSL values and area data, it may store PSL values per unit area and corrected PSL values per unit area.

Moreover, in the above described embodiment, although the image data are produced by using the stimulable phosphor sheet 1 and converting locational information regarding radioactive labeling substance to an electrical signal and are displayed on the CRT 60 as a visible image, it is possible to once form a visible image on a photographic film instead of the stimulable phosphor sheet 1, photoelectrically read the visible image, convert it to an electrical signal and process the thus obtained image data in a similar manner to the above.

Further, in the present invention, the respective means need not necessarily be physical means and arrangements whereby the functions of the respective means are accomplished by software fall within the scope of the present invention. In addition, the function of a single means may be accomplished by two or more physical means and the functions of two or more means may be accomplished by a single physical means.

According to the present invention, it is possible to provide an image analyzing apparatus which can accurately and smoothly quantitatively process and analyze an image contained in a region of interest defined by a pattern.

What is claimed is:

1. An image analyzing apparatus comprising image data storing means for storing image data, display means for displaying an image based on image data selected from the image data stored in the image data storing means and processed in a predetermined manner, graphic data storing means for storing graphic data corresponding to a plurality of patterns to be displayed on the display means, quantitative processing means for quantitatively processing image data corresponding to the images contained in regions of interest defined by the patterns, quantitative data storing means for storing quantitative data produced by the quantitative processing means, and background management means for producing and storing background data relating to background values corresponding to noise components for each of the patterns.

2. An image analyzing apparatus in accordance with claim 1 which further comprises background value producing means for producing the background values based on the background data stored in the background management means and the quantitative data stored in the quantitative data storing means and table data producing means for producing table data including the background value for each of the regions of interest and wherein the display means is adapted to display a table based on the table data.

3. An image analyzing apparatus in accordance with claim 2 wherein the background value producing means is adapted to produce density data of pixels constituting an image defined by the pattern and area data representing an area of the image and a reference background value per unit area based thereon, thereby producing the background value.

4. An image analyzing apparatus in accordance with claim 3 wherein in the case where the background value is produced using a plurality of patterns, the background value producing means is adapted to determine the reference background value by averaging the reference background values of the plurality of patterns.

5. An image analyzing apparatus in accordance with claim 1 wherein the graphic data storing means is adapted to store pattern numbers allotted to the patterns defining the regions of interest and the background management means comprises background storing means for storing a pattern number of the pattern defining the region of interest to be processed using the background value.

6. An image analyzing apparatus in accordance with claim 1 wherein the background management means is constituted so as to select graphic data corresponding to at least one pattern from the graphic data stored in the graphic data storing means and produce the background data based thereon to produce the background value.

7. An image analyzing apparatus in accordance with claim 6 wherein the background management means is adapted to allot a background number to the at least one pattern and the background storing means is adapted to store the pattern numbers in a region of the corresponding background number.

8. An image analyzing apparatus in accordance with claim 1 wherein the image data are produced using a stimulable phosphor sheet.

9. An image analyzing apparatus in accordance with claim 1 wherein the image data are constituted by image data selected from a group consisting of autoradiographic image data, radiographic diffraction image data, electron microscopic image data and chemiluminescent image data.

10. An image analyzing apparatus in accordance with claim 9 wherein the autoradiographic image data, the radiographic diffraction image data and the electron microscopic image data are produced by absorbing and storing the energy of a radiation or an electron beam emitted from a specimen in a stimulable phosphor, irradiating the stimulable phosphor with an electromagnetic wave and photoelectrically converting light emitted from the stimulable phosphor.

11. An image analyzing apparatus in accordance with claim 9 wherein the chemiluminescent image data are produced by absorbing and storing the energy of a visible light emitted from a specimen in a stimulable phosphor, irradiating the stimulable phosphor with an electromagnetic wave and photoelectrically converting light emitted from the stimulable phosphor.

12. An image analyzing apparatus comprising image data storing means for storing image data, display means for displaying an image based on image data selected from the image data stored in the image data storing means and processed in a predetermined manner, graphic data storing means for storing graphic data corresponding to a plurality of patterns to be displayed on the display means, quantitative processing means for quantitatively processing image data corresponding to the images contained in regions of interest defined by the patterns, quantitative data storing means for storing quantitative data produced by the quantitative processing means, and group data storing means for storing group data determined for showing the relationship between the patterns and groups to which the patterns belong.

13. An image analyzing apparatus in accordance with claim 12 which further comprises table data producing means for producing table data including a ratio of quantitative data for each of the groups based on the group data stored in the group data storing means and quantitative data stored in the quantitative data storing means and wherein the display means is adapted to display a table based on the table data.

14. An image analyzing apparatus in accordance with claim 12 wherein the graphic data storing means is adapted to store pattern number data allotted to the patterns defining the regions of interest and coordinate data showing positions of the patterns in the image data and the group data storing means is adapted to store the pattern number data of the patterns belonging to each of the groups.

15. An image analyzing apparatus in accordance with claim 14 wherein the table data producing means is adapted to produce table data for each of the groups and the display means is adapted to display a table based on the table data so that data are displayed for each of the pattern number data.

16. An image analyzing apparatus in accordance with claim 12 wherein the quantitative data produced by the quantitative data producing means comprise density data of pixels constituting images contained in regions of interest defined by the patterns and area data indicating areas of the regions defined by the patterns.

17. An image analyzing apparatus in accordance with claim 12 wherein the image data are produced using a stimulable phosphor sheet.

18. An image data analyzing apparatus in accordance with claim 12 wherein the image data are constituted by image data selected from a group consisting of autoradiographic image data, radiographic diffraction image data, electron microscopic image data and chemiluminescent image data.

19. An image analyzing apparatus in accordance with claim 18 wherein the autoradiographic image data, the radiographic diffraction image data and the electron microscopic image data are produced by absorbing and storing the energy of a radiation or an electron beam emitted from a specimen in a stimulable phosphor, irradiating the stimulable phosphor with an electromagnetic wave and photoelectrically converting light emitted from the stimulable phosphor.

20. An image data analyzing apparatus in accordance with claim 18 wherein the chemiluminescent image data are produced by absorbing and storing the energy of a visible light emitted from a specimen in a stimulable phosphor, irradiating the stimulable phosphor with an electromagnetic wave and photoelectrically converting light emitted from the stimulable phosphor.

21. An image analyzing method, comprising the steps of:
storing image data in an image storage;
displaying an image based on image data selected from the image data stored in the image storage;
storing graphic data corresponding to a plurality of patterns to be displayed;
quantitatively processing image data corresponding to images contained in regions of interest defined by said plurality of patterns;
storing quantitative data produced by the quantitative processing step; and
producing and storing background data relating to background values corresponding to noise components for each of said plurality of patterns.

22. The image analyzing method according to claim 21, further comprising the steps of:
producing the background values based on the background data and the quantitative data;
producing table data including the background value for each of the regions of interest; and
displaying a table based on the table data.

23. The image analyzing method according to claim 22, further comprising the steps of:
producing density data of pixels constituting an image defined by the pattern; and
producing area data representing an area of the image and a reference background value per unit area based thereon, thereby producing the background value.

24. The image analyzing method according to claim 23, further comprising the steps of:
producing the background value using a plurality of patterns; and
determining the reference background value by averaging the reference background values of the plurality of patterns.

25. The image analyzing method according to claim 21, further comprising the steps of:
  allotting pattern numbers to the patterns defining regions of interest; and
  storing a pattern number of the pattern defining the region of interest to be processed using the background value.

26. The image analyzing method according to claim 23, further comprising the steps of:
  allotting a background number to the at least one pattern; and storing the pattern numbers in a region of the corresponding background number.

27. The image analyzing method according to claim 21, further comprising the step of selecting graphic data corresponding to at least one pattern from the stored graphic data.

28. An image analyzing method, comprising the steps of:
  storing image data in an image storage;
  displaying an image based on image data selected from the image data stored in the image storage;
  storing graphic data corresponding to a plurality of patterns to be displayed;
  quantitatively processing image data corresponding to images contained in regions of interest defined by said plurality of patterns;
  storing quantitative data produced by the quantitative processing step; and
  storing group data determined for showing the relationship between the patterns and groups to which the patterns belong.

29. The image analyzing method according to claim 28, further comprising the steps of:
  producing table data including a ratio of quantitative data for each of the groups based on the group data and quantitative data; and
  displaying a table based on the table data.

30. The image analyzing method according to claim 28, further comprising the steps of:
  storing pattern number data allotted to the patterns defining the regions of interest;
  storing coordinate data showing positions of the patterns in the image data; and
  storing the pattern number data of the patterns belonging to each of the groups.

31. The image analyzing method according to claim 30, further comprising the steps of:
  producing table data for each of the groups; and
  displaying a table based on the table data so that data are displayed for each of the pattern number data.

* * * * *